(12) United States Patent
Pathak et al.

(10) Patent No.: US 11,867,892 B2
(45) Date of Patent: Jan. 9, 2024

(54) MINIATURE MICROSCOPE FOR MULTI-CONTRAST OPTICAL IMAGING IN ANIMALS

(71) Applicant: THE JOHNS HOPKINS UNIVERSITY, Baltimore, MD (US)

(72) Inventors: Arvind Pathak, Baltimore, MD (US); Nitish Thakor, Clarksville, MD (US); Janaka Senarathna, Baltimore, MD (US); Hang Yu, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 720 days.

(21) Appl. No.: 16/628,859

(22) PCT Filed: Jul. 6, 2018

(86) PCT No.: PCT/US2018/040979
§ 371 (c)(1),
(2) Date: Jan. 6, 2020

(87) PCT Pub. No.: WO2019/010348
PCT Pub. Date: Jan. 10, 2019

(65) Prior Publication Data
US 2020/0225457 A1    Jul. 16, 2020

Related U.S. Application Data

(60) Provisional application No. 62/529,100, filed on Jul. 6, 2017.

(51) Int. Cl.
*G02B 21/16* (2006.01)
*G02B 21/00* (2006.01)
(Continued)

(52) U.S. Cl.
CPC .............. *G02B 21/16* (2013.01); *A61B 5/002* (2013.01); *A61B 5/0042* (2013.01);
(Continued)

(58) Field of Classification Search
CPC ... A61B 5/0071; A61B 5/0261; A61B 5/0075; A61B 5/1455; A61B 5/002;
(Continued)

(56) References Cited

U.S. PATENT DOCUMENTS 7,304,789 B2    12/2007  Hirata et al.
8,788,021 B1     7/2014  Flusberg et al.
(Continued)

FOREIGN PATENT DOCUMENTS

JP    2016118792 A  *  6/2016  ........... A61B 5/0071
JP    2016118792 A     6/2016
(Continued)

OTHER PUBLICATIONS

Senarthna et al., A miniature multi-contrast microscope for functional imaging in freely behaving animals, Nature Communications, (2019)10:99| http: doi.org/10.1038/s41467-018-07926-z|www.nature.com/naturecommunications , pp. 1-13. (Year: 2019).*
(Continued)

*Primary Examiner* — Ishrat I Sherali

(57) ABSTRACT

An embodiment in accordance with the present invention provides a miniature microscope capable of performing in vivo, real-time imaging of multiple organ sites in awake and behaving animals (e.g. rodents). A microscope according to the present invention includes multiple optical contrast mechanisms (i.e. contrast arising from neural, hemodynamic and other physiological components). Exemplary contrast mechanisms include, but are not limited to fluorescence, hemoglobin level, deoxyhemoglobin level, and blood flow. The microscope is fully adaptable to in vitro and ex vivo (Continued)

imaging, can be customized to concurrently image at variable magnifications, conduct optogenetic/electrical/chemical stimulations, drug delivery, microdialysis, accompanied by electrical signal recording, wireless image transmission and charging.

21 Claims, 11 Drawing Sheets

(51) Int. Cl.
| | |
|---|---|
| H05B 47/19 | (2020.01) |
| A61B 5/00 | (2006.01) |
| A61B 5/1455 | (2006.01) |
| G02B 21/02 | (2006.01) |
| G02B 21/06 | (2006.01) |
| G02B 21/36 | (2006.01) |

(52) U.S. Cl.
CPC .......... *A61B 5/0071* (2013.01); *A61B 5/0077* (2013.01); *A61B 5/1455* (2013.01); *A61B 5/6814* (2013.01); *G02B 21/025* (2013.01); *G02B 21/06* (2013.01); *G02B 21/365* (2013.01); *H05B 47/19* (2020.01)

(58) Field of Classification Search
CPC ... A61B 5/0042; A61B 5/0077; A61B 5/6814; A61B 1/00; A61B 5/489; A61B 5/0084; H05B 47/19; G02B 21/16; G02B 21/025; G02B 21/365; G02B 21/082; G02B 21/06; G02B 21/0008
USPC .......................................... 382/128; 600/476
See application file for complete search history.

(56) References Cited

U.S. PATENT DOCUMENTS

| | | | |
|---|---|---|---|
| 9,448,394 | B2 | 9/2016 | Mandella et al. |
| 9,498,135 | B2 | 11/2016 | Ghosh et al. |
| 2007/0097494 | A1 | 5/2007 | Tokuda et al. |
| 2011/0033847 | A1 | 2/2011 | Walsh et al. |
| 2011/0125029 | A1 | 5/2011 | Wang et al. |
| 2011/0218432 | A1 | 9/2011 | Tumer |
| 2015/0309295 | A1 | 10/2015 | Cocker et al. |

FOREIGN PATENT DOCUMENTS

| | | |
|---|---|---|
| WO | 2012027586 A2 | 3/2012 |
| WO | 2015004968 A1 | 1/2015 |
| WO | 2016019458 A1 | 2/2016 |

OTHER PUBLICATIONS

Liao et al. et al., Neurovascular coupling in vivo optical techniques for functional brain imaging, BioMedical Engineering OnLine 2013, pp. 1-20. (Year: 2013).*
Luo, et al., Association between Hypoxia and Perinatal Arterial Ischemic Stroke: A Meta-Analysis. PLOS One. 2014; 9(2): e90106.
Jensen, Brain tumor hypoxia: tumorigenesis, angiogenesis, imaging, pseudoprogression, and as a therapeutic target. J Neurooncol. May 2009;92(3):317-35.
Frostig, et al., Cortical functional architecture and local coupling between neuronal activity and the microcirculation revealed by in vivo high-resolution optical imaging of intrinsic signals. Proc Natl Acad Sci U S A. Aug. 1990; 87(16): 6082-6086.
Tian, et al., Cortical depth-specific microvascular dilation underlies laminar differences in blood oxygenation level-dependent functional MRI signal. Proc Natl Acad Sci U S A. Aug. 24, 2010;107(34):15246-51.
Akemann, et al., Imaging brain electric signals with genetically targeted voltage-sensitive fluorescent proteins. Nature Methods. Jul. 2010; 7: 643-649.
Chen, et al., High-speed vascular dynamics of the hemodynamic response. Neuroimage. Jan. 15, 2011;54(2):1021-30.
Lee, et al., Relative changes of cerebral arterial and venous blood volumes during increased cerebral blood flow: implications for BOLD fMRI. Magn Reson Med. May 2001;45(5):791-800.
Tsukano, et al., Delineation of a frequency organized region isolated from the mouse primary auditory cortex. J Neurophysiol. Apr. 2015; 113(7): 2900-2920.
Deisseroth, Optogenetics. Nat Methods. Jan. 2011;8(1):26-9.
Ledochowitsch, et al., A transparent µECoG array for simultaneous recording and optogenetic stimulation. Conf Proc IEEE Eng Med Biol Soc. 2011;2011:2937-40.
Sigal, et al., Imaging brain activity during seizures in freely behaving rats using a miniature multi-modal imaging system. Biomed Opt Express. Sep. 1, 2016; 7(9): 3596-3609.
Flusberg, et al., In vivo brain imaging using a portable 3.9 gram two-photon fluorescence microendoscope. Optics Letters. Sep. 2005; 30(17): 2272-2274.
Helmchen, et al., A miniature head-mounted two-photon microscope. high-resolution brain imaging in freely moving animals. Neuron. Sep. 27, 2001;31(6):903-12.
Ringuette, et al., Multi-modal in vivo imaging of brain blood oxygenation, blood flow and neural calcium dynamics during acute seizures. Progress in Biometical Optics and Imaging—Proceedings of SPIE. 2016; 9690: 969011.
O'Herron, et al., Neural correlates of single-vessel haemodynamic responses in vivo. Nature. Jun. 16, 2016;534(7607):378-82.
Bouchard, et al., Ultra-fast multispectral optical imaging of cortical oxygenation, blood flow, and intracellular calcium dynamics. Opt Express. Aug. 31, 2009;17(18):15670-8.
Austin, et al., Confounding effects of anesthesia on functional activation in rodent brain: a study of halothane and alpha-chloralose anesthesia. Neuroimage. Jan. 1, 2005;24(1):92-100.
Ma, et al., Xenon mitigates isoflurane-induced neuronal apoptosis in the developing rodent brain. Anesthesiology. Apr. 2007;106(4):746-53.
Gad, et al., Miniature device for chronic, label-free multi-modal optical imaging of cortical hemodynamics in rats. Progress in Biomedical Optics and Imaging—Proceedings of SPIE. Feb. 2015; 9305: 93052H.
Sigal, et al., Chronic monitoring of cortical hemodynamics in behaving, freely-moving rats using a miniaturized head-mounted optical microscope. Progress in Biomedical Optics and Imaging—Proceedings of SPIE. Feb. 2016; 9690: 969010.
Ferezou, et al., Visualizing the cortical representation of whisker touch: voltage-sensitive dye imaging in freely moving mice. Neuron. May 18, 2006;50(4):617-29.
Ghosh, et al., Miniaturized integration of a fluorescence microscope. Nat Methods. Sep. 11, 2011;8(10):871-8.
Cantero, et al., Gamma EEG dynamics in neocortex and hippocampus during human wakefulness and sleep. Neuroimage. Jul. 2004;22(3):1271-80.
Ssa, et al., Multiscale optical Ca2+ imaging of tonal organization in mouse auditory cortex. Neuron. Aug. 20, 2014;83(4):944-59.
Rubinov, et al., Complex network measures of brain connectivity: uses and interpretations. Neuroimage. Sep. 2010;52(3):1059-69.
Hillman, Optical brain imaging in vivo: techniques and applications from animal to man. J Biomed Opt. Sep.-Oct. 2007;12(5):051402.
Senarthna, et al., Laser Speckle Contrast Imaging: theory, instrumentation and applications. IEEE Rev Biomed Eng. 2013;6:99-110.
Grinvald, et al., Functional architecture of cortex revealed by optical imaging of intrinsic signals. Nature. Nov. 27-Dec. 3, 1986;324(6095):361-4.
Tian, et al., Imaging neural activity in worms, flies and mice with improved GCaMP calcium indicators. Nat Methods. Dec. 2009; 6(12): 875-881.
Durduran, et al., Spatiotemporal quantification of cerebral blood flow during functional activation in rat somatosensory cortex using laser-speckle flowmetry. J Cereb Blood Flow Metab. May 2004;24(5):518-25.

(56) References Cited

OTHER PUBLICATIONS

Yaseen, et al., Multimodal optical imaging system for in vivo investigation of cerebral oxygen delivery and energy metabolism. Biomed Opt Express. Nov. 20, 2015;6(12):4994-5007.
Chen, et al., A critical role for the vascular endothelium in functional neurovascular coupling in the brain. J Am Heart Assoc. Jun. 12, 2014;3(3):e000787.
Bergonzi, et al., Mapping functional connectivity using cerebral blood flow in the mouse brain. J Cereb Blood Flow Metab. Mar. 2015,35(3):367-70.
Ba, et al., Multiwavelength optical intrinsic signal imaging of cortical spreading depression. J Neurophysiol. Nov. 2002;88(5):2726-35.
Sun, et al., Simultaneous monitoring of intracellular pH changes and hemodynamic response during cortical spreading depression by fluorescence-corrected multimodal optical imaging. Neuroimage. Aug. 1, 2011;57(3):873-84.
Yu, et al., Miniaturized optical neuroimaging in unrestrained animals. Neuroimage. Jun. 2015; 113:397-406.
Liu, et al., Extendable, miniaturized multi-modal optical imaging system: cortical hemodynamic observation in freely moving animals. Opt Express. Jan. 28, 2013;21(2):1911-24.
Munro, et al., Multi-modality optical neural imaging using coherence control of VCSELs. Opt Express. May 23, 2011;19(11):10747-61.
Miao, et al., Laser speckle contrast imaging of cerebral blood flow in freely moving animals. J Biomed Opt. Sep. 2011; 16(9):090502.
Lu, et al., Dual-modal (OIS/LSCI) imager of cerebral cortex in freely moving animals. Progress in Biomedical Optics and Imaging—Proceedings of SPIE. Mar. 2012; 8329: 83290P.
Park, et al., Head-mountable high speed camera for optical neural recording. J Neurosci Methods. Oct. 15, 2011;201(2):290-5.
Girouard, et al., Neurovascular coupling in the normal brain and in hypertension, stroke, and Alzheimer disease. J Appl Physiol (1985). Jan. 2006;100(1):328-35.
Logothetis, Neurovascular Uncoupling: Much Ado about Nothing. Front Neuroenergetics. Jun. 2, 2010;2.
Kalchenko, et al., Transcranial optical vascular imaging (TOVI) of cortical hemodynamics in mouse brain. Sci Reports. Jul. 2014; 4: 5839.
Hawkins, et al., Fluorescence imaging of blood-brain barrier disruption. J Neurosci Methods. Mar. 15, 2006;151(2):262-7.
Fukumura, et al., Hypoxia and acidosis independently up-regulate vascular endothelial growth factor transcription in brain tumors in vivo. Cancer Res. Aug. 15, 2001;61(16):6020-4.
Osman, et al., A head-mountable microscope for high-speed fluorescence brain imaging. 2011 IEEE Biomedical Circuits and Systems Conference (BioCAS). 2011; 114-116.
Dombeck, et al., Imaging large-scale neural activity with cellular resolution in awake, mobile mice. Neuron. Oct. 4, 2007;56(1):43-57.
Wekselblatt, et al., Large-scale imaging of cortical dynamics during sensory perception and behavior. J Neurophysiol. Jun. 1, 2016;115(6):2852-66.
Hillman, et al., Depth-resolved optical imaging and microscopy of vascular compartment dynamics during somatosensory stimulation. Neuroimage. Mar. 2007;35(1):89-104.
Hillman, Coupling mechanism and significance of the BOLD signal: a status report. Annu Rev Neurosci. 2014;37:161-81.
Stosiek, et al., In vivo two-photon calcium imaging of neuronal networks. Proc Natl Acad Sci U S A. Jun. 10, 2003;100(12):7319-24.
Smetters, et al., Detecting action potentials in neuronal populations with calcium imaging. Methods. Jun. 1999; 18(2):215-21.
Hirase, et al., Calcium Dynamics of Cortical Astrocytic Networks In Vivo. PLOS Biol. Apr. 2004; 2(4): e96.
Otsu, et al., Calcium dynamics in astrocyte processes during neurovascular coupling. Nat Neurosci. Feb. 2015; 18(2):210-8.
Hoffman, Green fluorescent protein imaging of tumour growth, metastasis, and angiogenesis in mouse models. Lancet Oncol. Sep. 2002;3(9):546-56.
Macdonald, et al., Detection of brain tumor invasion and micrometastasis in vivo by expression of enhanced green fluorescent protein. Neurosurgery. Dec. 1998;43(6):1437-42; discussion 1442-3.
Liu, et al., Carbon Nanotubes in Biology and Medicine: In vitro and in vivo Detection, Imaging and Drug Delivery. Nano Res. Feb. 1, 2009;2(2):85-120.
Vivero-Escoto, et al., Mesoporous silica nanoparticles for intracellular controlled drug delivery. Small. Sep. 20, 2010;6(18):1952-67.
Folkman, Role of angiogenesis in tumor growth and metastasis. Semin Oncol. Dec. 2002;29(6 Suppl 16):15-8.
Raghunand, et al., Microenvironmental and cellular consequences of altered blood flow in tumours. Br J Radiol. 2003;76 Spec No. 1:S11-22.
Armitage, et al., Laser speckle contrast imaging of collateral blood flow during acute ischemic stroke. J Cereb Blood Flow Metab. Aug. 2010; 30(8): 1432-1436.
Parthasarathy, et al., Quantitative imaging of ischemic stroke through thinned skull in mice with Multi Exposure Speckle Imaging. Biomed Opt Express. Jul. 15, 2010;1(1):246-259.

* cited by examiner

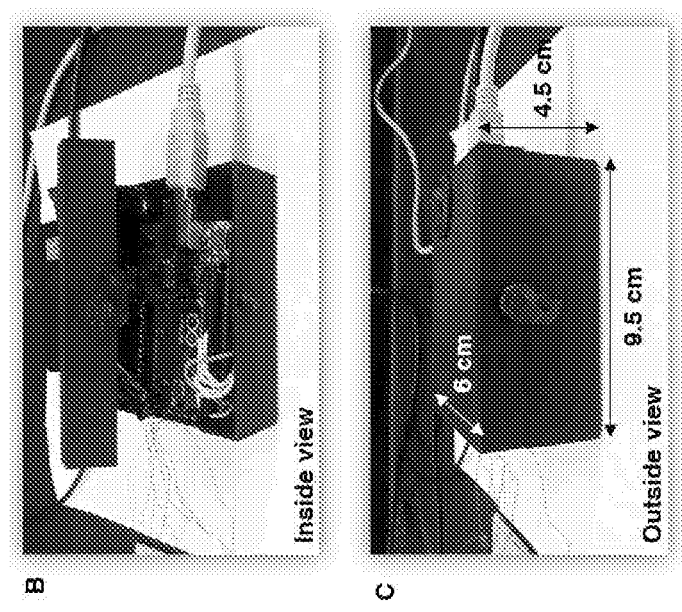
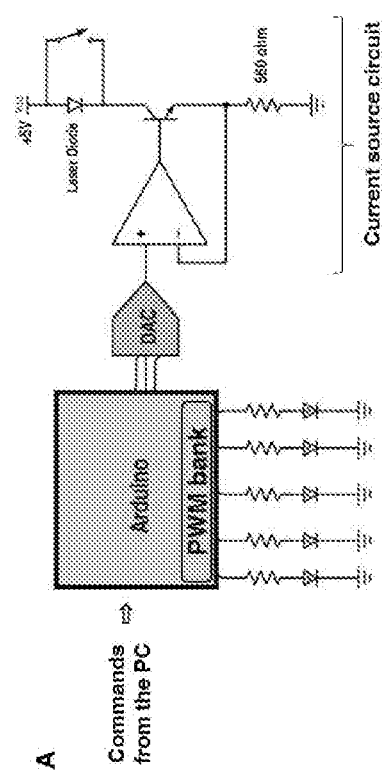
FIGS. 3A-3C

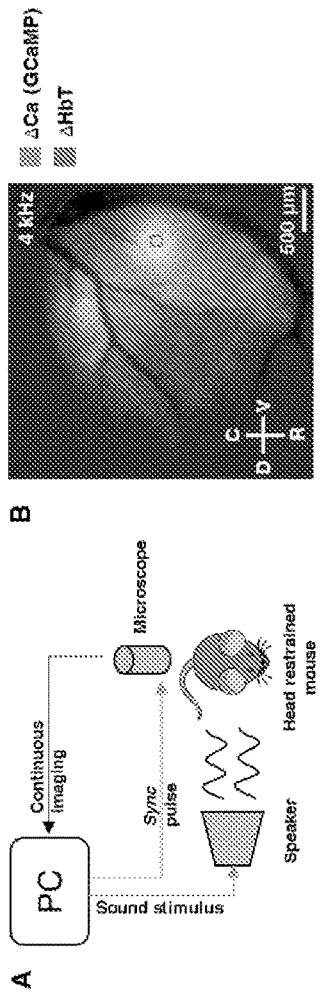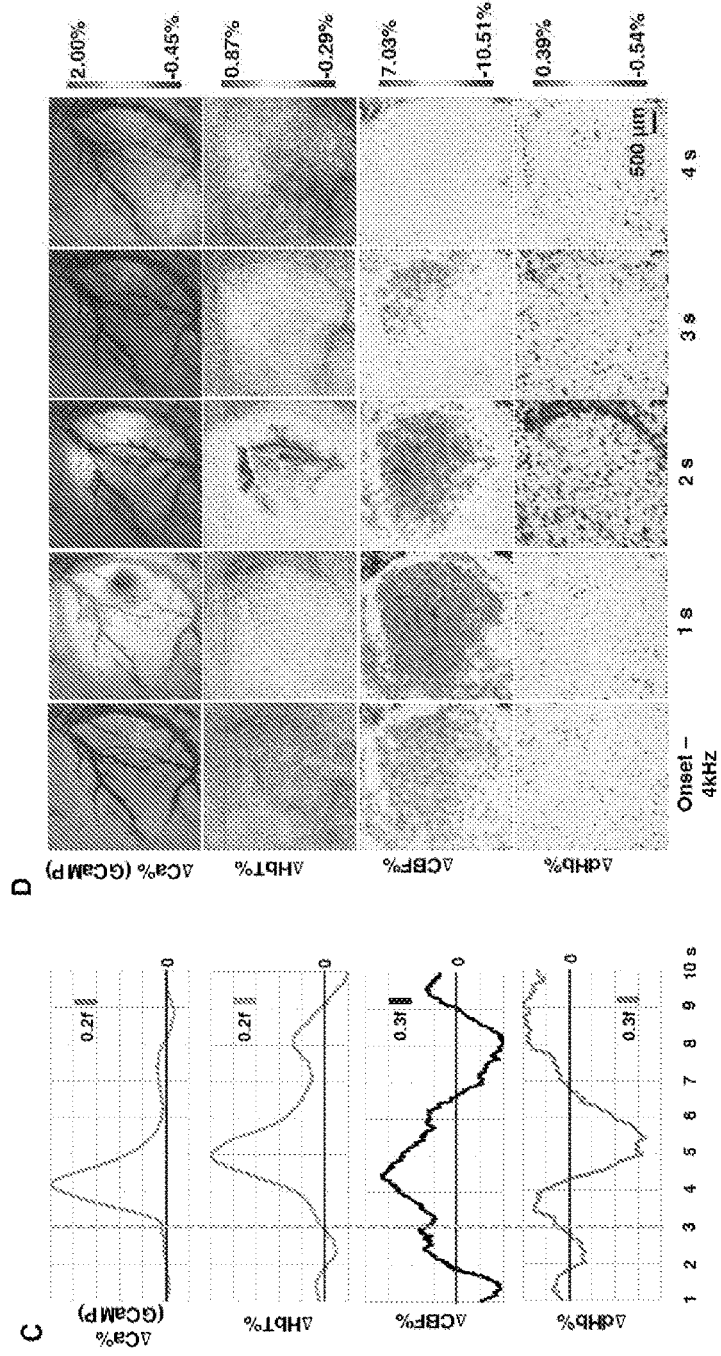
FIGS. 6A-6D

MINIATURE MICROSCOPE FOR MULTI-CONTRAST OPTICAL IMAGING IN ANIMALS

CROSS-REFERENCE TO RELATED APPLICATIONS

This application is a 35 U.S.C. § 371 U.S. national entry of International Application PCT/US2018/040979, having an international filing date of Jul. 6, 2018, which claims the benefit of U.S. Provisional Application No. 62/529,100, filed Jul. 6, 2017, the content of each of the aforementioned applications is herein incorporated by reference in their entirety.

GOVERNMENT SUPPORT

This invention was made with government support under grant number 1R21CA175784-01 awarded by the National Institutes of Health. The government has certain rights in the invention.

FIELD OF THE INVENTION

The present invention relates generally to imaging devices. More particularly, the present invention relates to a miniature microscope for multi-contrast (e.g. contrast arising from neural, hemodynamic or other physiologic components) optical imaging in animals or in vitro preparations such as cellular or perfusion assays.

BACKGROUND OF THE INVENTION

Brain function involves the interplay between many biological variables (e.g. a complex set of interactions between neurons, blood vessels, astrocytes etc.). Therefore, to better understand brain function and its disruption by disease, one needs a tool for simultaneously tracking/quantifying these biological variables in vivo. Optical imaging is the tool of choice for interrogating these variables over a wide field-of-view with high spatial resolution in preclinical or animal models. However, most traditional in vivo optical imaging systems employ a single image contrast mechanism (e.g. fluorescence) and are therefore capable of interrogating only a single biological or physiological variable at a time. Recently, multi-contrast optical imaging systems have been developed that permit the concurrent interrogation of multiple neurophysiological variables in vivo.

Imaging the brain in vivo with multiple optical contrast mechanisms, i.e. in vivo multi-contrast neuroimaging enables one to study the brain more holistically rather than one neurophysiological variable at a time. This approach would permit in-depth investigations of healthy brain function as well as brain dysfunction (i.e. disease) enabling better characterization of the underlying physiology or neuro-circuitry. Moreover, this approach can also assist in finding cures to debilitating neuropathologies or testing and validating the efficacy of novel therapeutics.

The need to combine multiple optical contrast mechanisms often requires a custom-built imaging system with bulky hardware and optical components. This makes most multi-contrast neuroimaging systems non-portable, precluding their use in a wide variety of in vivo experiments in freely moving or unanesthetized animals. Such experiments include those relating behavior to neural activity or those that require continuous imaging for extended durations (e.g., days). Additionally, since brain function is significantly affected by the use of anesthetics it is desirable to conduct such experiments in unanesthetized animals, without the confounding effects of anesthetics. Finally, the bulkiness of conventional multi-contrast imaging systems limits the number of contrast mechanisms that can be realized in one system, and also restricts the recording of additional neurophysiological variables such as electrophysiology and neurochemical recordings. These hurdles have created a need for affordable, convenient and portable multi-contrast neuroimaging systems.

In response to this unmet need, several miniaturized neuroimaging microscope designs capable of awake animal imaging have recently been developed. However, currently available imaging systems are limited to performing either neural or hemodynamic imaging, but not both. This in turn has limited in viva experiments in awake animals to those that interrogate either the brain's neuronal or vascular function, but not both. For example, several miniature microscope designs that combine intrinsic optical signal (IOS) imaging and laser speckle contrast (LSC) imaging have been reported. These microscopes combine data on endogenous hemoglobin dynamics acquired with IOS imaging, and blood flow dynamics acquired using LSC imaging. However, they lack the ability to directly interrogate neural function, which requires the ability to image fluorescence (FL). Miniature microscopes that also have a fluorescence (FL) contrast module or channel could overcome this limitation by permitting the imaging of calcium dynamics with fluorescent GCaMP reporters or of membrane potential with voltage sensitive dyes. However, due to technical limitations, current miniature microscopes that have a FL channel do not perform IOS and LSC imaging.

Therefore, it would be advantageous to have a miniature microscope capable of performing multi-contrast imaging in awake, freely behaving animals.

SUMMARY OF THE INVENTION

The foregoing needs are completely met by the present invention, wherein in one aspect a device for wide-field optical imaging includes a microscope for multi-contrast imaging, including a base unit, wherein the base unit comprises the illumination sources configured for generating conditions needed for multi-contrast imaging. The microscope also includes an upper unit, wherein the upper unit comprises a lens configuration for image formation, an optical filter, a focusing mechanism, and an image sensor.

In accordance with an aspect of the present invention, the microscope further includes the optical filter being configured for cutting off blue fluorescent excitation light. The illumination sources include at least one selected from a group of a blue LED, a green LED, a laser diode, and an orange LED. The green LED can take the form of two green LEDs and the orange LED can take the form of two orange LEDs. The microscope can further include a head mount for mounting the microscope on the head of a subject animal.

In accordance with another aspect of the present invention, the microscope includes custom-built mounts for mounting the microscope on different body locations (e.g. the head, spine, mammary fat pad etc.) of a subject animal. The microscope includes an adapter for variable magnification imaging. The microscope includes a wireless module for data transmission and tether-free operation. The microscope includes integrated circuits or very-large-scale integration (VLSI) fabricated chips with an on-board image sensor and modules for hardware encoded image processing and wireless transmission.

In accordance with yet another aspect of the present invention, the microscope includes a remote master controller. The remote master controller takes the form of a laptop, tablet, smart phone or suitable peripheral device for controlling imaging and illumination parameters. The remote master controller is coupled to the microscope via a wire bundle. The remote master controller is coupled to the microscope via a wireless connection. The microscope includes an illumination controller for controlling the illumination sources. The illumination controller is coupled to the microscope via a wired connection. The illumination controller is coupled to the microscope via a wireless connection. The wireless connection takes the form of WiFi or Bluetooth® or any other custom/commercial wireless connectivity protocol.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIGS. 3A-3C illustrates the illumination control module, according to an embodiment of the present invention.

FIGS. 6A-6D illustrate schematic, image, and graphical views of functional multi-contrast brain imaging in the awake murine auditory cortex, according to an embodiment of the present invention.

FIGS. 9A-9SE illustrate image and graphical views of the design of a wireless multi-contrast microscope, according to an embodiment of the present invention.

DETAILED DESCRIPTION

Figures 1A, 1B, 1C, 1D, 1E, 1F, 1G, 1H:
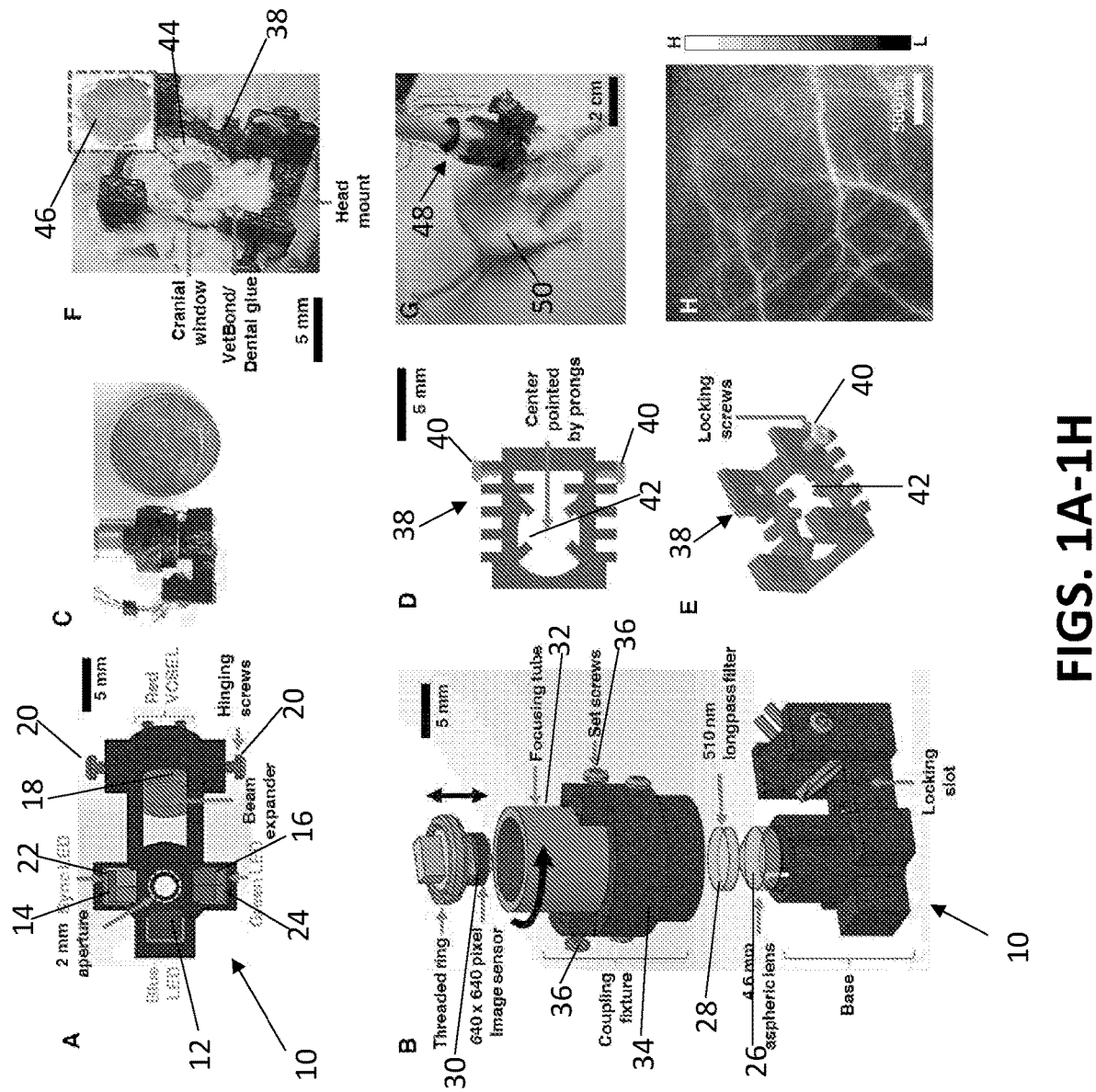
FIGS. 1A-1H illustrates perspective and image views of microscope construction, according to an embodiment of the present invention.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

LIST OF ABBREVIATIONS

IOS: Intrinsic Optical Signals
LSC: Laser Speckle Contrast
CBF: Cerebral Blood Flow
HbT: Total hemoglobin
dHb: deoxy hemoglobin
LED: Light Emitting Diode
GFP: Green Fluorescence Protein
FITC: Fluorescein Isothiocyanate
VCSEL: Vertical Cavity Surface Emitting Laser
MCP: Master Control Program
FoV: Field of View
DAC: Digital to Analog Converter An embodiment in accordance with the present invention provides a miniature multi-contrast (i.e. contrast arising from neural and hemodynamic components) microscope capable of performing in vivo, real-time imaging of multiple organ sites in awake (i.e. unanesthetized) and freely behaving rodents. A microscope according to the present invention includes multiple optical contrast mechanisms. Exemplary contrast mechanisms include, but are not limited to fluorescence, absorption by hemoglobin (by each of oxy- and deoxy-forms), and laser speckle contrast due to blood flow. The present embodiment provides multi-contrast imaging of four biological variables in vivo: (i) Neural activity (via GCaMP fluorescence or other fluorescent reporter); (ii) total hemoglobin level (via IOS at 570 nm); (iii) deoxyhemoglobin level (via IOS at 680 nm); and (iv) blood flow (via LSC).

Previous miniaturized microscopes could either image only hemodynamic changes or neural activity, but not both. Miniaturized microscopes designed for hemodynamic imaging were confined to using hemodynamic data as a surrogate to neural activity. In contrast, previous miniaturized microscopes designed for neural imaging could only acquire neural activity data and not the accompanying hemodynamic changes. By incorporating a (green or other) fluorescence channel in addition to two forms of hemodynamic imaging, our microscope is able to capture neural activity (via GCaMP imaging of calcium fluorescence or some other fluorescent indicator) or cellular imaging (via fluorescence expression) and its corresponding hemodynamics (via HbT, dHb absorption and laser speckle contrast based blood flow).

The microscope is fully adaptable and can be customized to simultaneously conduct optogenetic stimulations, drug delivery, microdialysis, and wireless image transmission and charging.

The present invention provides wide field multi-contrast imaging. Wide field refers to the ability to image a large area at once (as opposed to scanning techniques like two photon or confocal imaging that image a single spot at any given time). The microscope of the present invention images a wide field of view (FoV)=3×3 mm$^2$ with an in-plane spatial resolution equal to 5 µm. (N.B. Both the field of view and the spatial resolution can be changed as desired by modifying the microscope's optical components). In contrast, prior miniaturized fluorescence microscopes were typically confined to imaging smaller (i.e. sub-mm) FoVs. Therefore, this microscope permits imaging neural and hemodynamic changes over larger spatial extents than was previously possible. Currently, wide field images can be acquired at the rate of 15 frames per second. This can be improved by incorporating a faster image acquisition module (i.e. sensor and/or camera).

Moreover, the present invention provides a high magnification adaptor to the microscope which improves its spatial resolution by 10×, while the FoV is 300×300 µm$^2$. As mentioned above, this microscope can image FL, IOS and LSC and has the ability to interrogate both neural and hemodynamic activity, i.e. neurovascular coupling, in a variety of settings ranging from functional imaging to brain connectivity as well as the loss of neurovascular coupling in neuropathologies such as stroke, neurodegenerative diseases, and brain cancer or metastasis. Moreover, the FL module, when not used to observe neural activity, could be used in a multiple ways to supplement IOS/LSC based hemodynamic measures, i.e., to distinguish arterial from venous blood flow following an intravenous injection of a fluorescent tracer, to assess blood-brain-barrier (BBB) integrity as well as to visualize the progression of fluorescently tagged tumors etc.

Moreover, such a miniature multi-contrast microscope could be used to image not just the brain, but any part of the animal's body. E.g. the spinal cord, the liver/kidney or even the mammary fat pat etc. In addition, such imaging can be readily expanded beyond in vivo (i.e. live animal) studies too ex vivo (i.e. in excised animal body parts) as well as in vitro (i.e. in chemically prepared brain slices, cell cultures, microfluidic devices etc.) biological studies. Additionally, such a microscope may find applications in multi-contrast imaging of non-biological samples as well (e.g. biomaterials of various kinds).

Finally, such a microscope could be used for both acute (i.e. a single imaging session lasting hours or less) or chronic (i.e. imaging continuously over days, weeks or months) imaging tasks. Specifically, chronic imaging with this microscope would be useful for: studying the etiology, evolution and progression of preclinical disease models (e.g. brain cancer, stroke etc.), fundamental neuroscientific applications (e.g. studying neural plasticity or connectivity in the awake/anesthetized brain, optogenetics, or correlating neural circuits/substrates with animal behavior), testing novel therapies, drug delivery, and treatment efficacy in preclinical models.

A microscope according to the present invention includes a very compact microscope assembly. The microscope of the present invention weighs 9 g and occupies 5 cm$^3$. The present invention is also suitable for imaging in awake and behaving rodents (i.e. mice and rats). Many parts of the microscope of the present invention were fabricated using rapid prototyping and 3D printing technologies. This permits customization of the entire system to suit the application at hand. For example, in a preferred embodiment the microscope supports three concurrent optical contrast mechanisms. The microscope includes disposable housing parts and custom-fabricated head/organ-mounts to interface the microscope with the animal's brain (or other organ) in a robust and repeatable manner. The microscope is portable and can be moved easily to accommodate different imaging needs. Portability can be further enhanced in the next generation of microscopes by using wireless image transmission and charging.

A small supplementary illumination controller module allows microscope light sources to be controlled without the need for an external current source instrument. Both the microscope's image acquisition module and the illumination controller module are powered by their USB connections to a personal computer (or laptop), thereby eliminating the need for an external power source. An in-built synchronization module (also powered via a USB connector to the personal computer) permits synchronization of the microscope recordings with additional external instruments. For example, in some instances a preferred embodiment of the present invention can include synchronizing image acquisition with EEG (i.e. electrophysiological) recording. This principle could be expanded to synchronize image acquisition with optogenetic stimulations, drug delivery, microdialysis and/or wireless image transmission.

To facilitate ease of use, the present invention also includes a convenient 'one-stop' graphical user interface (GUI) for all interactions with the microscope and supplementary control modules. This GUI can run on any personal computer or suitable computing device (e.g. a tablet or smart phone) known to or conceivable to one of skill in the art. A platform independent graphical user interface is also included within the scope of the present invention.

FIGS. 1A-1H illustrate perspective and image views of microscope construction, according to an embodiment of the present invention. FIG. 1A illustrates a perspective view of a microscope base unit, according to an embodiment of the present invention. The base unit 10 contains all of the light sources necessary for multi-contrast imaging. Excitation for fluorescence imaging of GFP/FITC is provided by a blue LED 12 with a wavelength range of 452±13 nm (Osram Opto Semiconductors, LD CNSM-1R1S-35-1-Z). Intrinsic optical signal (IOS) imaging of HbT absorption is accomplished by using a pair of green LEDs 14, 16 with 570 nm±20 nm illumination (Broadcom, HSMF-C157). A miniature 680 nm VCSEL diode (Vixar, IO-680S-0000-B093), assisted by a 6 mm focal length concave lens (Anchor optics, 27753) for beam expansion 18 and a pair of hinging screws 20 (McMaster-Carr, 96710A050) for fine-tuning laser spot location, facilitates both IOS imaging of dHb absorption and laser speckle contrast (LSC). Any other suitable combination and/or configuration of illumination sources known to or conceivable by one of skill in the art could also be used. Indeed, in some of the embodiments all of the light sources are customizable based on the application and can be swapped out as required. For example, in some embodiments one of the LEDs can be replaced with a red/near infra-red (NIR) LED for NIR imaging. Moreover, the blue LED can be replaced with a different colored LED for excitation of a different fluorescent moiety for which the optical filter in the microscope upper unit will be changed accordingly. A separate pair of orange colored LEDs 22, 24 (as part of Broadcom, HSMF-C157 package) is used for synchronizing the microscope with physiological recording or stimulation systems. The FoV of 3×3 mm$^2$ being imaged lies directly underneath the 2 mm aperture.

FIG. 1B illustrates a perspective, exploded view of the microscope upper unit (shown together with the base). A 6 mm diameter, 4.6 mm focal length aspheric lens 26 (Thorlabs, A-390) is used to focus light with a magnification of 0.75. A 510 nm, 1 mm thick optical long-pass filter 28 (Omega Optical, 510ALP) selectively excludes blue excitation light. A 640×640 pixel grayscale image sensor 30 (CMOSIS, NanEyeGS) is used to acquire images. The 3.6 µm pitch pixels with 10 bit digital resolution facilitate high resolution image acquisition at speeds up to 15 frames per second. The image sensor 30 is mounted on a focusing tube 32 (Thorlabs, AD8T) attached to a custom built coupling 34, that allows its position to be varied vertically to achieve focus. A pair of set screws 36 (McMaster-Carr, 96710A050) locks the image sensor in position once focusing has been achieved. The image magnification and image acquisition frame rate can be customized based on the application as required by modifying the optical components. Although not shown, the image sensor is attached via a wire bundle to an image acquisition module (Idule image acquisition module, CMOSIS).

Both microscope units were rapid prototyped with ABSplus material using a 3D printer (Stratasys, Dimension bst1200es). The current realization of the microscope weights 9 g and occupies 5 cm$^3$.

FIG. 1C illustrates a perspective view of the microscope assembly and a quarter coin for appreciating the scale of the miniaturization, according to an embodiment of the present invention. 3D printing permits the customization of the entire system to suit the application at hand. The weight and size of the microscope could be reduced further in the future when lighter materials for 3D printing and smaller miniaturized components become commercially available. An exemplary prototype supports three simultaneous optical contrast mechanisms. This prototype could be easily fabricated to simultaneously conduct optogenetic stimulations, drug delivery, microdialysis and/or wireless image transmission and charging. 3D prototyping makes the microscope of the present invention adaptable to a wide array of applications.

FIGS. 1D and 1E illustrate a bottom view and a side view of the head mount, respectively, according to an embodiment of the present invention. The head mount 38 is implanted on a surgically exposed animal skull (or organ), and enables the microscope to firmly attach via a pair of locking screws 40 (McMaster-Carr, 96710A050). The prong structure 42 at the bottom face of the head mount allows it to be centered on the surgically prepared FoV at the time of implantation. Friction between the microscope base and the head mount assists the locking screws in holding the microscope in place.

FIG. 1F illustrates such a head mount 38 attached to a mouse skull 44. The inset shows the cranial window preparation that provides optical access to the mouse brain 46. FIG. 1G shows a pictorial representation of the microscope 48 attached to an awake and freely behaving mouse 50, while FIG. 1H shows an LSC based CBF map. Scale bars indicate length where applicable. 3D printing permits the customization of the mount to suit the organ site being imaged in a given application/experiment. For example, a mount appropriate for imaging the ear or the mammary fat pad could also be printed. A microscope 'kit' could come with a number of mounts for a common set of applications/experiments. While a mouse brain is being imaged in the examples herein, any other organ or study animal known to or conceivable to one of skill in the art could be used.

Figures 2A, 2B:
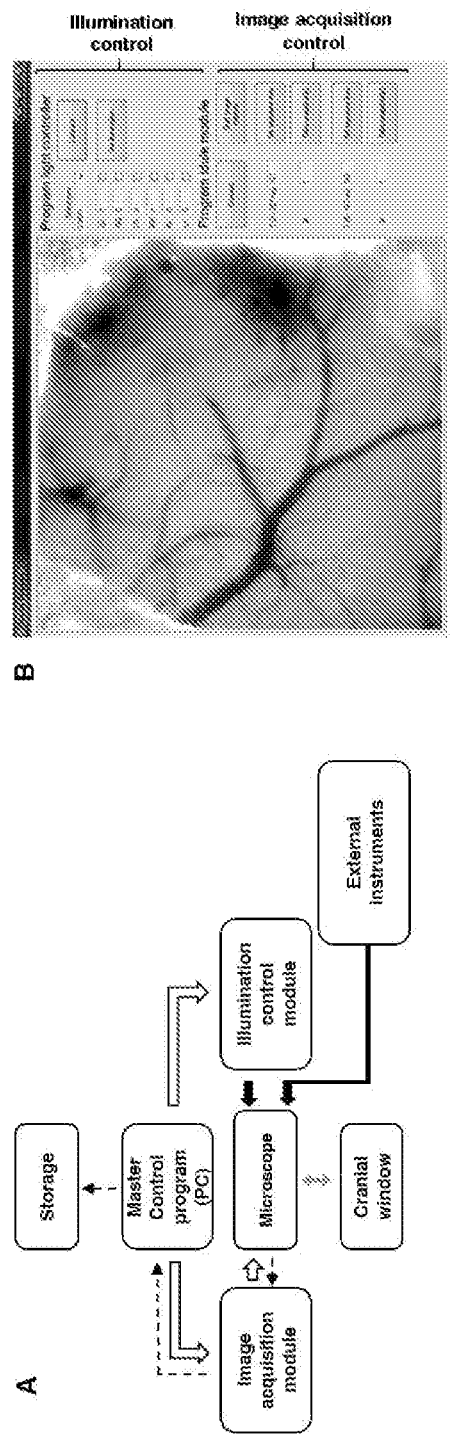
FIGS. 2A and 2B illustrate a schematic diagram of the computer software process and an image of the graphical user interface (GUI), according to an embodiment of the present invention.

FIGS. 2A and 2B illustrate a schematic diagram of the computer software process and an image view of the graphical user interface (GUI), according to an embodiment of the present invention. The system architecture for microscope control is shown in FIG. 2A. Digital communication is indicated by hollow arrows while analog current supply is shown by a thick arrow. Light illumination of and the collection from the cranial window by the microscope is represented by a double sided green arrow. The flow of acquired images from the microscope through the image acquisition module, the master controller program until the storage medium is shown by dashed arrows.

A master control program (MCP) running on a personal computer (PC) or other computing device known to or conceivable to one of skill in the art plays the role of a central hub to all control and data flow. Manual user inputs are provided to the MCP via the GUI, as illustrated in FIG. 2B.

As illustrated in FIG. 2A, the illumination levels necessary for each light source are communicated by the MCP to the illumination controller, which in turn drives each light sources accordingly. The MCP also communicates with the image acquisition module (CMOSIS, Idule module) to set the exposure time of the image sensor, as well as initiate image capture. The image acquisition module then interacts with the image sensor (CMOSIS, NanEyeGS) to acquire and transfer images back to the MCP for eventual storage. Each stored image is digitally labeled with a 'time stamp' with millisecond accuracy. Image processing is carried out offline.

FIGS. 3A-3C illustrate the illumination control module, according to an embodiment of the present invention. FIG. 3A illustrates a schematic diagram of the system architecture. Commands from the MCP residing in the PC are sent to a microcontroller (an Arduino Uno) via USB communication. Accordingly, the microcontroller activates either the PWM modules or the DAC. If LED illumination is desired, a combination of three separate PWM modules is activated: one each for the blue LED, and the left and right green LEDs. In the case of laser illumination, the DAC (Microchip, MCP4821) creates an analog voltage, which is converted into a steady current level by the op-amp/transistor circuit, which then delivers the current through the laser diode. Current levels of up to 5 mA are used to drive the blue LED, while the green LEDs each require a maximum of 20 mA. The laser is driven by a 2-3 mA current. FIGS. 3B and 3C illustrate physical dimensions via image views.

Figures 4A, 4B, 4C:
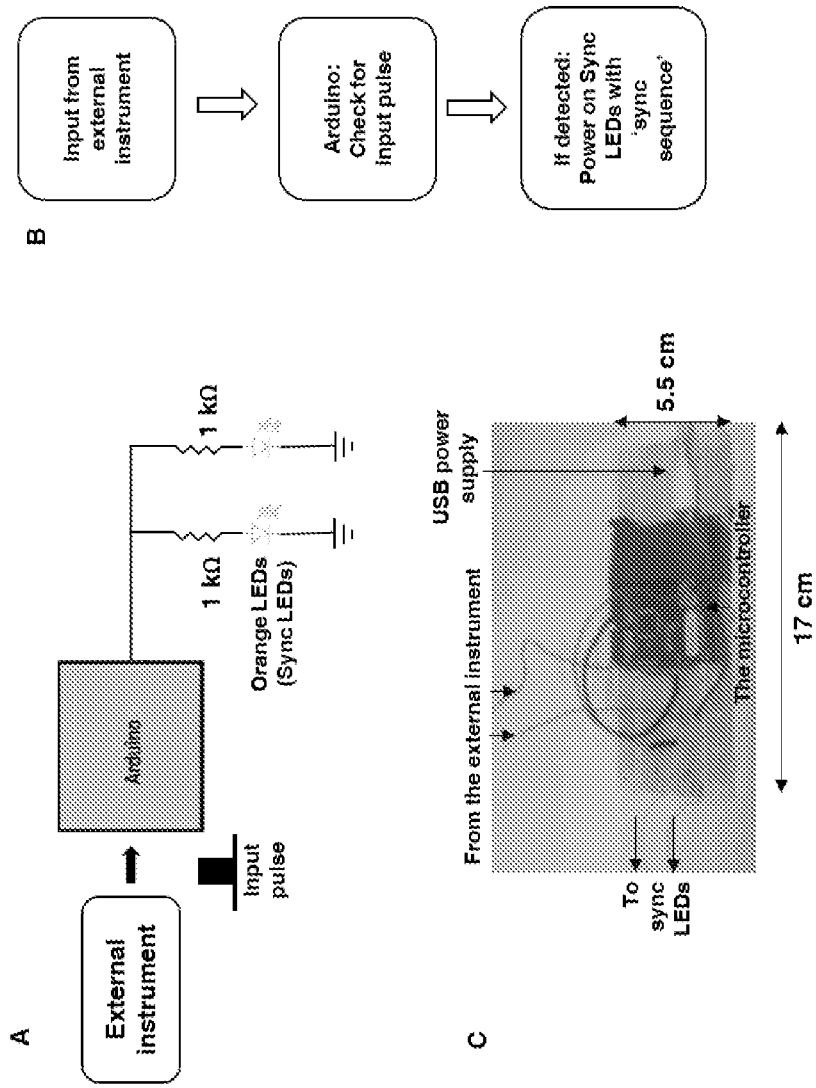
FIGS. 4A-4C illustrates schematic and image views of the synchronization module, according to an embodiment of the present invention.

FIGS. 4A-4C illustrate schematic and image views of the synchronization module, according to an embodiment of the present invention. FIG. 4A illustrates a schematic diagram of the system architecture, FIG. 4B illustrates the work flow inside the microcontroller, and FIG. 4C illustrates dimensions via an image. The synchronization module consists of a pulse detection algorithm coded on a microcontroller (Arduino, Uno), as illustrated in FIG. 4B. It detects the output sync pulse from any external recording instrument or hardware. The microcontroller loops continuously while monitoring the input. If a change in input from digital low to high is detected, the synchronization LEDs (orange LEDs) are powered in a pre-programed manner. In the current implementation, it is set to: LEDs ON for 100 ms—LEDs OFF for 100 ms LEDs ON for 100 ms—LEDs OFF. The synchronization wavelength, sequence and rate can be customized as required based on the application.

Figures 5A, 5B, 5C, 5D, 5E, 5F, 5G, 5H, 5I, 5J, 5K:
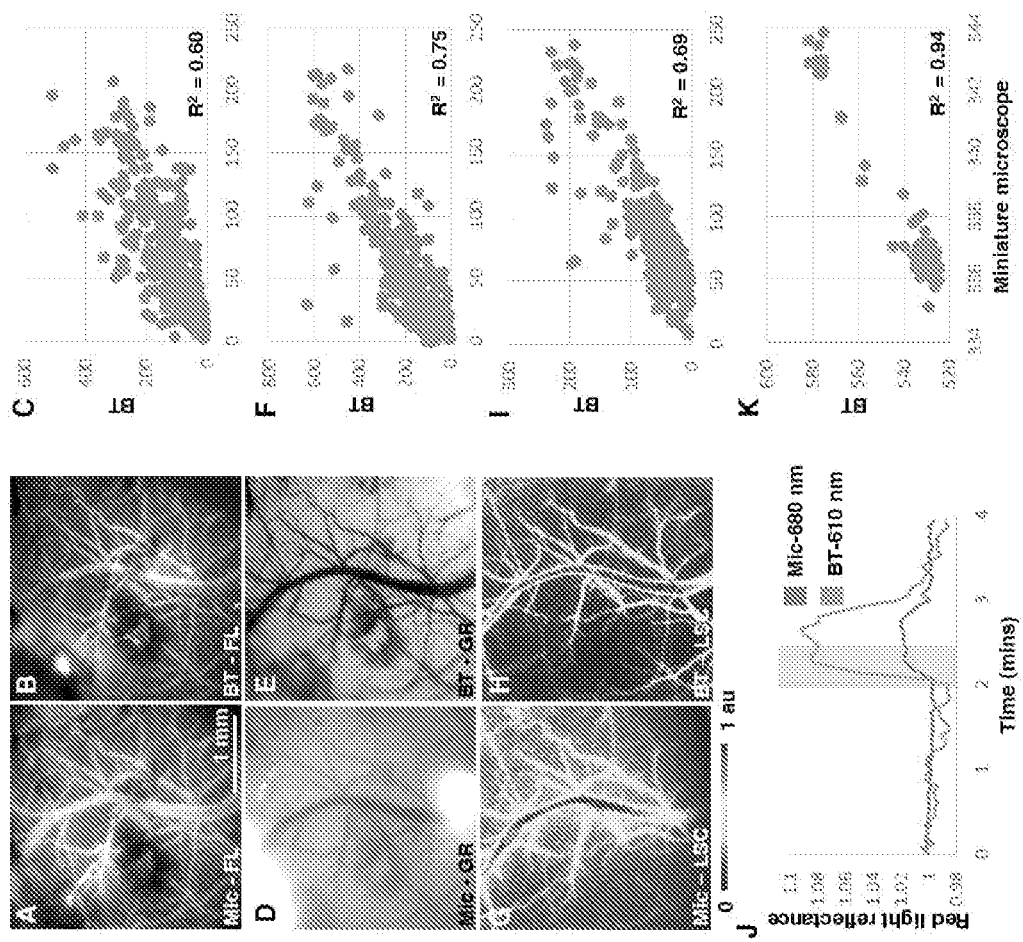
FIGS. 5A-5K illustrates image and graphical views of validation of microscope performance, according to an embodiment of the present invention.

FIGS. 5A-5K illustrate image and graphical views of validation of microscope performance, according to an embodiment of the present invention. FIGS. 5A, 5B, 5D, 5E, 5G, and 5H illustrate images of a mouse brain obtained from the microscope (MIC) and a similarly equipped benchtop (BT) imaging system. FIGS. 5A and 5B illustrate a network of microvessels visualized with fluorescent imaging (FL) after a tail vein injection of FITC-dextran dye. FIGS. 5D and 5E illustrate the same FoV imaged using green IOS (GR) capturing the extent of HbT. FIGS. 5G and 5H illustrate pseudocolored maps of relative CBF obtained by performing speckle contrast under laser illumination (LSC). Time courses of dHb dependent red light reflectance within a central 20×20 pixel window in response to an oxygen gas inhalation challenge (30 s starting at 2 mins and room air for the rest of the duration). FIGS. 5C, 5F, 5I, and 5K illustrate graphical views of corresponding scatter plots and correlation values ($R^2$). Correlation values ($R^2$) of 0.60, 0.75 and 0.69 were observed, respectively. The high correlation values indicate the reliability of the microscope for conducting in vivo imaging using each of the four contrast mechanisms.

FIGS. 6A-6D illustrate schematic, image, and graphical views of functional multi-contrast brain imaging, according to an embodiment of the present invention. FIG. 6A illustrates an experimental setup. FIG. 6B illustrates a false colored map showing the maximum calcium response (pseudocolored in green) and its corresponding maximum vasodilatory response (pseudocolored in red) to 4 kHz stimulation. Anatomical directions dorsal (D)—ventral (V), caudal (C)—rostral (R) are shown for reference. A vessel mask underlay is used for clarity. FIG. 6C illustrates time traces of calcium and hemodynamic transients to 4 kHz stimulus in the 20×20 pixel area marked in FIG. 6B. Units are in fractions (f) of peak response. The horizontal black line indicates the baseline mean of each trace. A sliding window of 1 s was used for smoothing all data. Therefore, the 10 s trial, where a 300 ms auditory stimulus was delivered at 3 s, is shown from to 1 s to 10 s. FIG. 6D illustrates time-lapsed snapshots capturing the spatiotemporal evolution of the neurovascular response to 4 kHz stimulation. All image sequences are normalized to 0.1% of range before extracting snapshots. A 3×3 pixel median filter was used for noise reduction. The CBF and dHb images are smoothed by an additional 20×20 pixel window before normalization for further reduction of noise. A vessel mask underlay is used in the first raw of images for clarity.

Figures 7A, 7B, 7C, 7D:
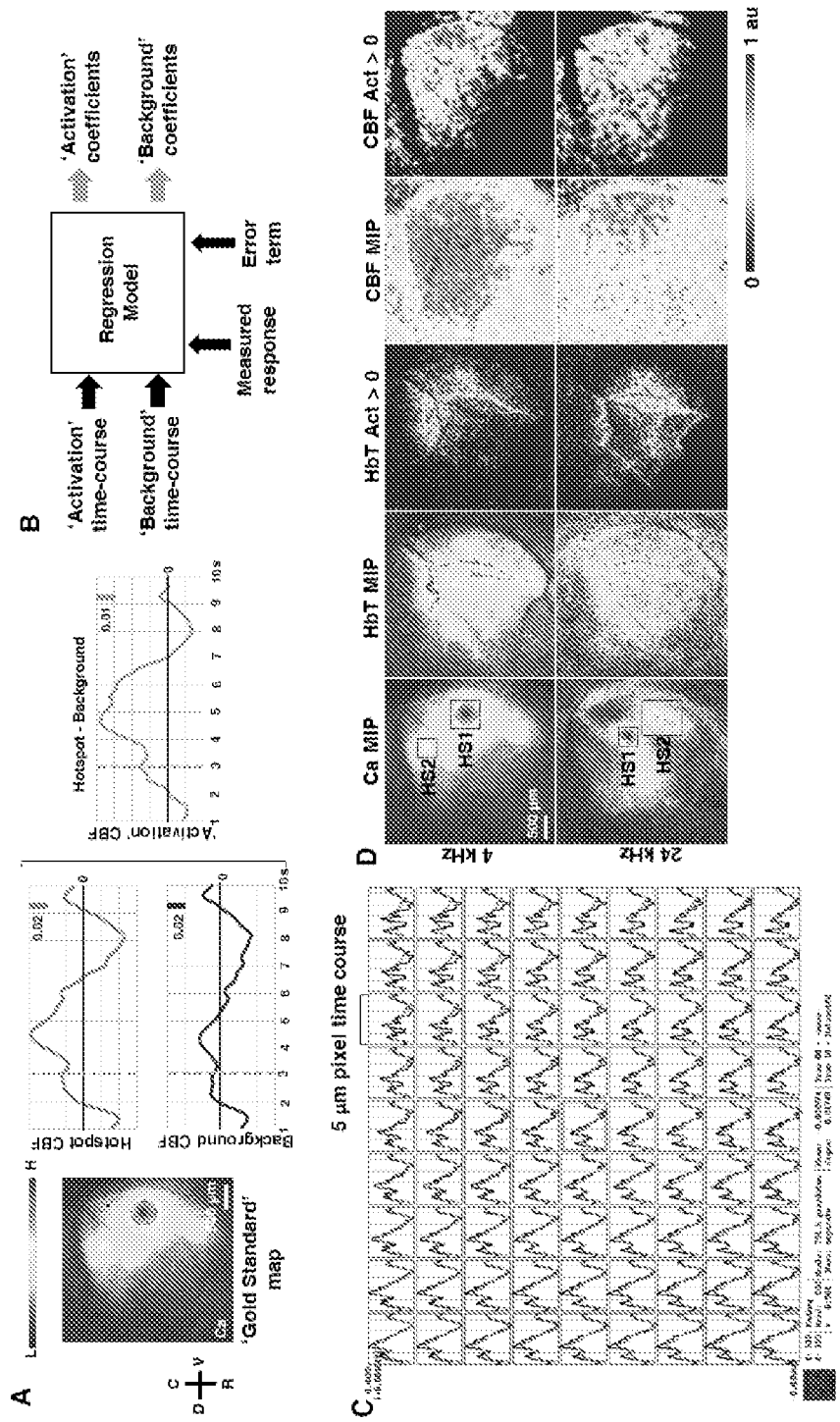
FIGS. 7A-7D illustrate image and graphical views of a wide area functional optical mapping of the awake murine brain analogous to functional Magnetic Resonance Imaging (fMRI), according to an embodiment of the present invention.

FIGS. 7A-7D illustrate image and graphical views of a wide area functional optical mapping of the awake murine brain analogous to fMRI, according to an embodiment of the present invention. FIGS. 7A-7B illustrate how the calcium response is used as a gold standard to calculate stimulus dependent 'activation coefficients' for the hemodynamic responses. As illustrated in FIG. 7A, the maximal calcium response to a 4 kHz tone permits identification of a 'hotspot', showing the region with the highest calcium response (marked by the dotted circle). The ensuing analysis is explained by using the CBF signal as an example. A 'hotspot' CBF time series can be computed by taking the average CBF response for this region. Similarly, by computing the average CBF signal over the entire FoV, yields a 'background' CBF time series. Finally, an 'activation' time series can be created by subtracting the background time series from the hotspot time series.

FIG. 7B illustrates the linear regression model used to calculate the activation coefficients. Both the activation and background time series serve as the inputs to the regression model. Next, the activation and background coefficients are computed for each pixel by fitting a linear combination of the two input time series to the measured response time series for that pixel. As illustrated in FIG. 7C, the measured (black) and fit (grey) time series show the accuracy of the regression model. A 9×9 pixel area in the small black box marked in FIG. 7A is shown here to demonstrate the quality of the model fitting at the scale of individual pixels. FIG. 7D shows a comparison of the maximum neural firing (calcium), vasodilation (HbT) and CBF response patterns to both 4 kHz and 24 kHz stimulations. Hashed black boxes mark activation 'hotspots' (HS1 and HS2) in each of the calcium images and are in agreement with previously reported studies. The ability to map and compare both neural and hemodynamic changes in an awake animal using a miniaturized microscope is an optical "first" and constitutes a powerful new tool for neuroscientific applications.

The microscope of the present invention can also be used in an exemplary implementation for distinguishing between vessel compliance and flow dynamics during arousal from anesthesia. Vessel compliance (i.e. vasodilation/vasoconstriction) and cerebral blood flow (i.e. CBF) are assumed to be causally linked. However, independently interrogating each can reveal their exact relationship and how they are altered by disease and/or therapy. Green light IOS and LSC channels of the microscope were used for this experiment. A cranial window over the right hemisphere of a mouse was surgically created. The microscope was used to acquire distinct vessel compliance-blood flow profiles at the spatial scale of individual cortical microvessels over a three hour period as the mouse regained consciousness from deep anesthesia. Variations in vessel HbT absorption imaged with green light IOS were used to assess alterations in vessel compliance, while LSC provided a dedicated measure of CBF changes. Moreover, concurrent EEG recordings were acquired from the contralateral hemisphere. The EEG recording device was synchronized with the microscope acquisition using the microscope's dedicated 'sync' channel. This allowed EEG recording of electrophysiological activity to be time-locked to the hemodynamic data acquisition.

Figures 8A, 8B, 8C, 8D, 8E, 8F, 8G:
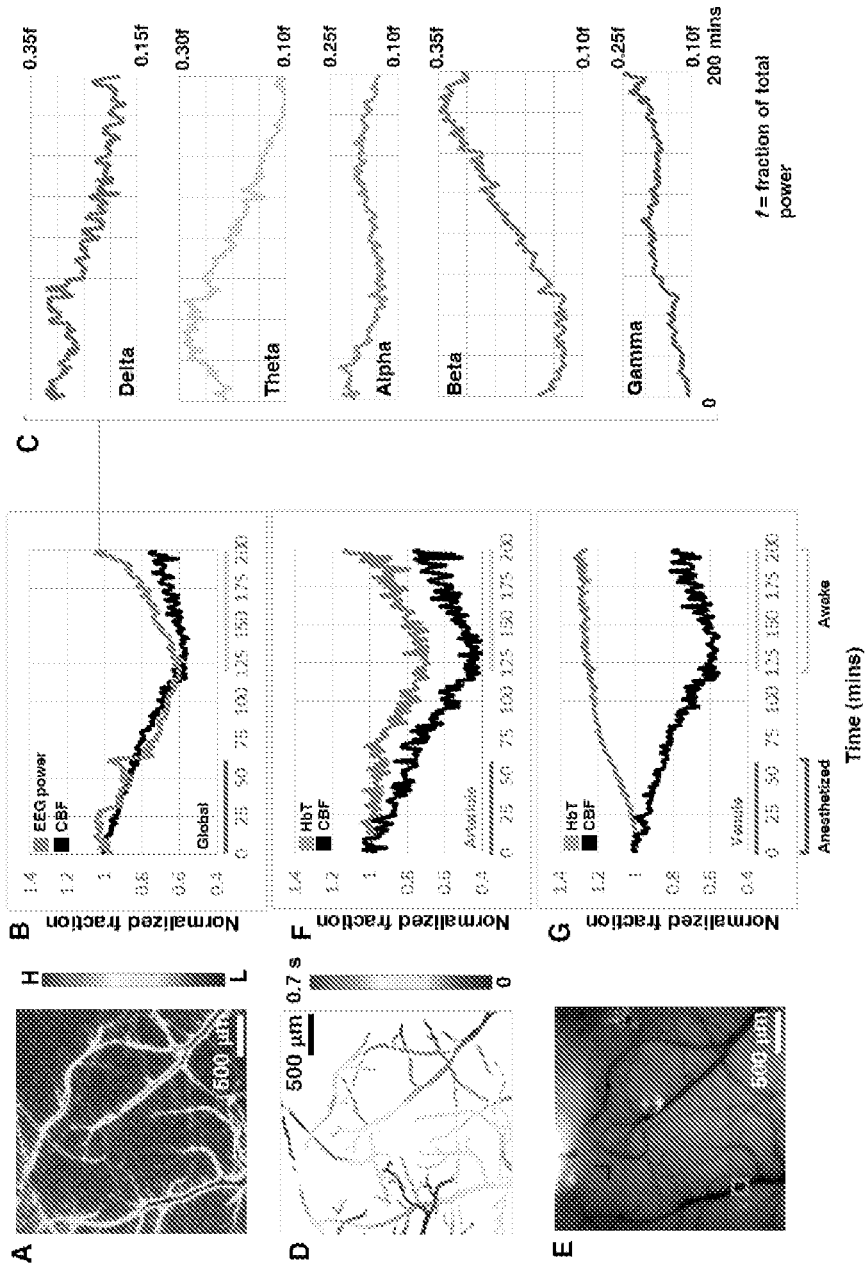
FIGS. 8A-8G illustrates image and graphical views distinguishing between vessel compliance and flow dynamics during arousal from anesthesia as well as time-locked EEG recordings via the 'sync' channel, according to an embodiment of the present invention.

FIGS. 8A-8G illustrates this experiment, according to an embodiment of the present invention. FIG. 8A illustrates pseudocolored CBF map showing the FoV. The variation of global CBF (i.e. CBF averaged over the entire FoV) and EEG power is shown in FIG. 8B. As illustrated, the two quantities are highly correlated ($R^2=0.70$). FIG. 8C shows the breakdown of the EEG power into the standard sub-bands delta, theta, alpha, beta and gamma. It can be seen that none of the sub-band powers show a correlation with global CBF. FIG. 8D shows a pseudocolored map showing delays in the tail vein injected FITC fluorescence signal. All times are indicated relative to the earliest appearance of fluorescence with the FoV. FIG. 8E shows a an IOS image acquired under green light illumination of the same FoV with an arterial (A) and venous (V) region indicated. FIGS. 8F-8H show the HbT and CBF time-courses for the artery and vein segments, respectively. Anesthetized and awake phases are marked by colored bars. As illustrated by FIG. 8F, the artery exhibits tight coupling between vessel compliance and blood flow, i.e. an initial vasoconstrictive phase accompanied by a drop in CBF and a vasodilatory phase accompanied with a rise in CBF. However, the venous region did not exhibit a similar coupling between vascular compliance and CBF, as illustrated in FIG. 8G.

Figures 9A, 9B, 9C, 9D, 9E:
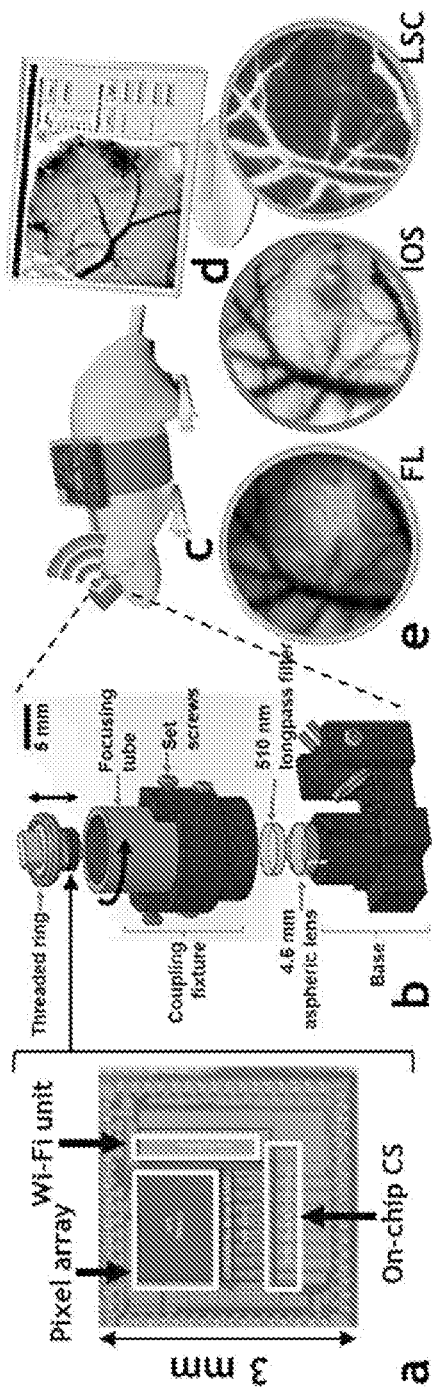

FIGS. 9A-9E illustrate image and graphical views of the design of a wireless multi-contrast microscope, according to an embodiment of the present invention. Here, FIG. 9A shows a CMOS sensor with in-built compressed sensing (CS) and Wi-Fi transmission capabilities. This approach can be extended to include any "hardware level" image processing and any form of wireless connectivity. FIG. 9B shows a schematic of the miniature microscope with fluorescence, intrinsic optical signals, and laser speckle contrast channels. FIG. 9C shows a schematic of an awake mouse bearing the wireless microscope and rodent backpack (i.e. controllers and battery). FIG. 9D shows a custom-built graphical user interface (GUI) for real-time imaging. FIG. 9E shows in vivo images (~5 µm resolution) of a brain tumor obtained using the FL channel, blood vessel structure or cerebral blood volume (CBV) obtained using the IOS channel, and cerebral blood flow (CBF) obtained using the LSC channel in an awake, brain tumor-bearing mouse using the tethered version of the miniaturized microscope.

Figures 10A, 10B, 10C, 10D:
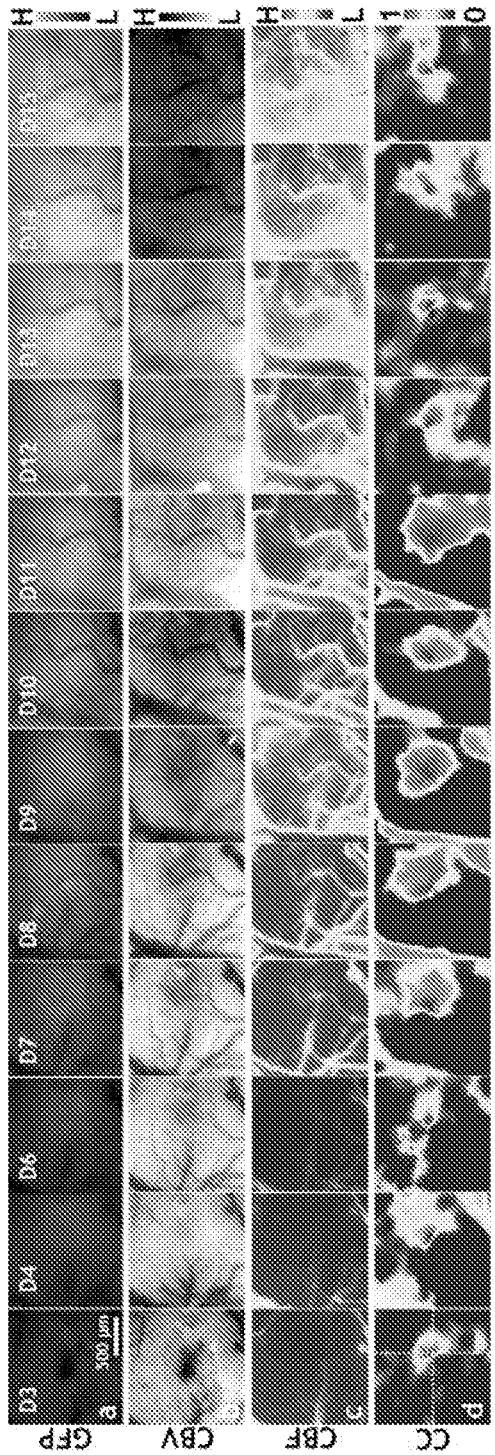
FIGS. 10A-10D illustrate image views of chronic (i.e. lifetime or life cycle) imaging of a brain tumor's vasculome, according to an embodiment of the present invention.

FIGS. 10A-10D illustrate image views of chronic (i.e. lifetime or life-cycle) imaging of a brain tumor model, according to an embodiment of the present invention. Here, multichannel images starting from day 3 (D3) until day 15 (D15) of: tumor progression (i.e. GFP fluorescence), as illustrated in FIG. 10A; angiogenesis (i.e. CBV changes assessed with IOS), as illustrated in FIG. 10B; perfusion (i.e. CBF changes assessed with LSC), as illustrated in FIG. 10C; and microvascular connectivity changes assessed using CBV fluctuations for a seed vessel segment near the tumor inoculation site (indicated by cross-hairs), as illustrated in FIG. 10D. Image sequences are normalized to 1% of their intensity range. CBV-based cross correlation coefficient (CC) maps were smoothed and positive CC values displayed. Scale bar=500 µm.

Figures 11A, 11B, 11C, 11D, 11E:
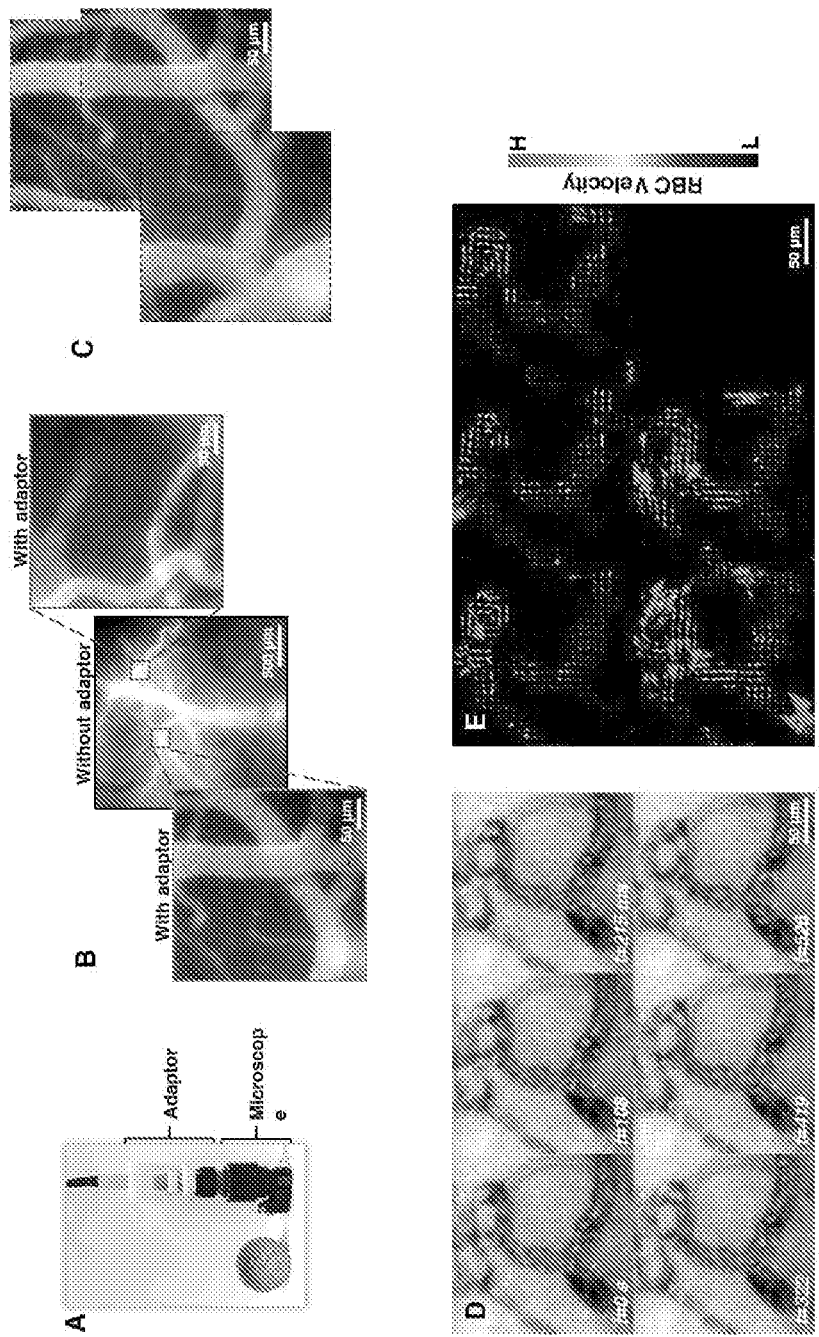
FIGS. 11A-11E illustrate image and graphical views detailing the design and application of a high-magnification adaptor for the miniaturized microscope, according to an embodiment of the present invention.

FIGS. 11A-11E illustrate image and graphical views detailing the design and application of a high magnification adaptor for the miniaturized microscope, according to an embodiment of the present invention. FIG. 11A shows the microscope with the high-magnification adaptor alongside a U.S. quarter coin for scale. FIG. 11B shows an image of fluorescent dye enhanced murine cortical vasculature. Insets are magnified fields of view obtained with the adaptor. FIG. 11C shows a high-magnification mosaic stitched together from three different fields of view. Images in FIGS. 11B and 11C are normalized to 1% of their intensity ranges. FIG. 11D shows high magnification video frames from a fluorescent-dye enhanced blood vessel network from the mouse ear in which the red blood cells (RBCs) have been highlighted in red. One can clearly visualize the motion of individual RBCs over time in each vessel segment, from which one can conduct particle velocimetry and compute the direction and magnitude of RBC flux as shown in FIG. 11E.

General image processing steps used in the above applications are described below.

Laser speckle contrast (LSC) is calculated by processing a stack of red laser images. The speckle contrast (k) at each pixel (x, y) is calculated as:

$$k(x, y) = \frac{\sigma(x, y)}{\mu(x, y)} \quad (1)$$

Here µ and σ are the mean and standard deviation of light intensity at each pixel in the chosen image stack. The image stack size depends on the frame rate and temporal resolution desired for the LSC image. i.e. with 15 Frames per second, a 4 s time resolution will allow a stack of 60 images. The speckle contrast (k) is related to blood flow speed by:

$$k^2 = \frac{\tau}{2T}\left\{2 - \frac{\tau}{T}\left[1 - \exp\left(-\frac{2T}{\tau}\right)\right]\right\} \quad (2)$$

Here exposure time is denoted by T, and τ denotes a quantity termed decorrelation coefficient, a quantity inversely proportional to blood flow speed. For small τ values (associated with typical microcirculation imaged by the microscope), eq. 2 can be simplified to:

$$\frac{1}{\tau} \propto \frac{1}{k^2} \quad (3)$$

Eq. 3 was thus used to compute CBF in all the experiments.

Calcium and hemodynamic responses were calculated as below in the optical functional imaging experiment (FIGS. 6 and 7):

$$r(t) = \frac{x(t) - \bar{x}_B}{\bar{x}_B} \quad (4)$$

Here, r(t) is the calculated response, x(t) the measured variable, and $\bar{x}_B$ is the baseline (1-3 s) mean of the measured variable. In the case of calcium fluorescence imaging, the light reflectance levels were taken as the measured variable. For HbT and dHb imaging, inverted green light and red laser light images were used respectively, while the relative blood flow levels calculated by LSC were used for CBF.

In the arousal from anesthesia experiment, the 'time-to-appear' map (FIG. 8D) was constructed for the fluorescent tracer by counting the time until the signal reached 20% of its peak value. The time values were then referenced to the earliest time-to-appear for the entire field of view, thereby creating a tracer delay map. Arterial-venous categorization was then carried out by observing a) the delay value, where a low delay value would imply a high probability of arterial flow, and b) pattern of delay values at branch points, where the delay will increase when moving from a parent vessel to its branches under arterial flow and vice versa under venous flow.

The hemodynamic signals in the arousal from anesthesia experiment were calculated by removing the effect of two factors: (a) the underlying 'background' signal, and (b) incident illumination intensity fluctuations. The underlying background signal was removed by applying a background subtraction filter (ImageJ, 50 pixel radius). The green light IOS images were inverted before subtracting the background. In the case of LSC Flow images, background was directly subtracted. Fluctuations in illumination intensity affected only the absorption images. LSC Flow images are immune to incident intensity variations. Therefore, the background subtracted inverted green IOS images were divided by an indicator of the incident illumination level. A heavily smoothed version of the non-inverted green IOS image (100×100 pixel) was chosen as an approximation for the incident light level.

Cross correlation maps in the tumor lifetime imaging experiment (FIG. 10) were calculated as follows. First, images were recorded with 1 s resolution for 5 mins. All time traces underwent bandpass filtering of 0.01-0.1 Hz. Then, the time trace of the region identified by the cross hairs was used as a reference trace to calculate cross correlation for the time trace of each and every pixel in the FoV.

Furthermore, at least one of the light sources can be used as a synchronization channel between an external module (i.e. an additional recording instrument) and the microscope. This is accomplished by the external module generating a brief pulse that turns on the said illumination source, which is then imaged by the microscope for synchronization with external recording instruments.

In addition, the microscope can be connected to a remote master controller (i.e. a laptop/tablet/smart phone or suitable peripheral device for controlling imaging and illumination parameters) via either a wire bundle (i.e. tethered) or via a wireless connection (e.g. Wi-Fi or other communications protocol).

When a wire bundle is used to connect the microscope to a remote master controller, a subset of wires will connect the image sensor to an image acquisition module, while the microscope illumination sources are connected to a separate illumination controller module. These two control modules are connected to the remote master controller through an additional set of wires (e.g. via USB or similar standard electronic connectors).

Where wireless connectivity is used, two options are possible. First, miniature illumination/acquisition control modules are mounted in an animal backpack or flexible electronic substrate that wraps around the rodent. Then, the controllers connect via a WiFi (or suitable wireless communication protocol) network to the remote master controller. Power is provided via a battery (e.g. a Li-poly 100 mA battery) included in this backpack. Alternatively, the said control modules could be miniaturized using Very Large Scale Integration (VLSI) technology into an integrated circuit together with the image sensor. In this realization, the backpack will only house the small battery or alternative power source (e.g. solar cells).

Furthermore, such a microscope could incorporate different magnification levels (enabling different levels of spatial resolution) to interrogate physiology at spatial scales ranging from the whole organ to individual cells. For example, a 5 μm spatial resolution would allow imaging microvascular networks over a large cortical region (e.g. 3×3 mm$^2$) while a 0.5 μm resolution could enable imaging activity of individual cells.

Different image processing algorithms such as laser speckle contrasting, compressed sensing etc., could be directly implemented in the image sensor circuitry (e.g. VLSI chip) or controller circuitry to increase data acquisition and transmission efficiency. The wireless transmission module could also be incorporated on the same VLSI integrated circuit or chip.

Changes can be made to the microscope of the present invention, as would be known to or conceivable by one of skill in the art. For instance a tri-modal laser diode could be used to improve estimation of oxygenation. An optogenetic simulation LED could equip the microscope with the capacity to excite or inhibit neural activity while performing concurrent multi-contrast imaging. The cranial window preparation could also be expanded to permit extended functionality. For instance, a transparent electrocorticographic ECoG grid within the cranial window would allow direct access to neural activity while freeing the microscope's fluorescent channel to image an additional biological process. The cranial window could also be supplemented with a delivery channel for administering chemical agents or therapeutics providing a direct input for pharmacological intervention within the field of view being interrogated.

The many features and advantages of the invention are apparent from the detailed specifications, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A microscope for multi-contrast in vivo/ex vivo/in vitro imaging, comprising:
   a base unit, wherein the base unit comprises illumination sources configured for generating conditions needed for multi-contrast imaging, wherein the illumination sources are configured to allow simultaneous imaging of neural activity, total hemoglobin level, deoxyhemoglobin level, and blood flow;
   an upper unit, wherein the upper unit comprises a lens configuration for image formation, an optical filter, a focusing mechanism, and an image sensor.

2. The microscope of claim 1 further comprising the optical filter being configured for cutting off fluorescent excitation light.

3. The microscope of claim 1 wherein the illumination sources comprise at least one selected from a group consisting of a blue LED, a green LED, a laser diode, and an orange LED.

4. The microscope of claim 3 wherein the green LED comprises two green LEDs.

5. The microscope of claim 3 wherein the orange LED comprises two orange LEDs.

6. The microscope of claim 1 further comprising a head mount for mounting the microscope on a head of a subject animal.

7. The microscope of claim 1 further comprising other custom-built mounts for mounting the microscope on other body locations of a subject animal.

8. The microscope of claim 1 further comprising an adapter for variable magnification imaging.

9. The microscope of claim 1 further comprising a wireless module for data transmission and tether-free operation.

10. The microscope of claim 1 further comprising integrated circuits or very-large-scale integration (VLSI) fabricated chips with an on-board image sensor and modules for hardware encoded image processing and wireless transmission.

11. The microscope of claim 1 further comprising a remote master controller.

12. The microscope of claim 11 wherein the remote master controller takes a form of a laptop, tablet, smart phone or suitable peripheral device for controlling image acquisition, image processing, image transmission, image storage and illumination parameters.

13. The microscope of claim 11 wherein the remote master controller is coupled to the microscope via a wire bundle.

14. The microscope of claim 11 wherein the remote master controller is coupled to the microscope via a wireless connection.

15. The microscope of claim 14 wherein the wireless connection takes a form of WiFi or Bluetooth®-protocol wireless connection or any other custom or commercial wireless connectivity protocol.

16. The microscope of claim 1 further comprising an illumination controller for controlling the illumination sources.

17. The microscope of claim 16 wherein the illumination controller is coupled to the remote master controller via a wired connection.

18. The microscope of claim 16 wherein the illumination controller is coupled to the remote master controller via a wireless connection.

19. The microscope of claim 18 wherein the wireless connection takes the form of WiFi or Bluetooth®-protocol wireless connection or any other custom or commercial wireless connectivity type.

20. The microscope of claim 1 further comprising the illumination source taking a form of a synchronization channel between an external module and the microscope.

21. The microscope of claim 1 wherein the illumination sources take the form of a fluorescence reporter, an intrinsic optical signal imager, and laser special contrast.

* * * * *